United States Patent [19]
Bundgaard et al.

[11] Patent Number: 5,908,846
[45] Date of Patent: Jun. 1, 1999

[54] TOPICAL COMPOSITIONS FOR TRANSDERMAL DELIVERY OF PRODRUG DERIVATIVES OF MORPHINE

[75] Inventors: Hans Bundgaard, deceased, late of Hörsholm, by Charlotte Bundgaard, legal representative; Lona Christrup, Brönshöj; Jörn Drustrup, Köpenhamn; Ann Fullerton, Vanlöse, all of Denmark; Martin Nicklasson, Södertälje, Sweden

[73] Assignee: Pharmacia & Upjohn AB, Stockholm, Sweden

[21] Appl. No.: 08/050,336

[22] PCT Filed: Nov. 11, 1991

[86] PCT No.: PCT/SE91/00760

§ 371 Date: Aug. 17, 1993

§ 102(e) Date: Aug. 17, 1993

[87] PCT Pub. No.: WO92/08459

PCT Pub. Date: May 29, 1992

[51] Int. Cl.$^6$ ............... A61K 31/485; A61K 47/00; A61K 9/70
[52] U.S. Cl. ............ 514/282; 514/946; 514/947; 514/817
[58] Field of Search ............... 514/282, 946, 514/947, 817

[56] References Cited

U.S. PATENT DOCUMENTS

| | | | |
|---|---|---|---|
| 4,673,679 | 6/1987 | Aungst et al. | 514/282 |
| 4,879,297 | 11/1989 | Mahjour et al. | 514/282 |
| 4,891,377 | 1/1990 | Shipman, Jr. et al. | 514/282 |
| 4,908,389 | 3/1990 | Mahjour et al. | 514/282 |
| 4,940,586 | 7/1990 | Cheng et al. | 514/282 |
| 5,240,932 | 8/1993 | Morimoto et al. | 514/282 |

FOREIGN PATENT DOCUMENTS 0 171 742 A2  2/1986  European Pat. Off. .

OTHER PUBLICATIONS

Roy, et al., Transdermal Delivery of Narcotic Analgesics: Comparative Permeabilities of Narcotic Analgesics Through Human Cadaver Skin, Pharmaceutical Research, vol. 6, No. 10 (1989), pp. 825–832.

Rieg–Falson, et al., Characterization of the Enhancing Effect of a Vehicle in a Transdermal System, Drug Development and Industrial Pharmacy, 15(14–16) (1989), pp. 2393–2406.

Sloan, Prodrugs for dermal delivery, Advanced Drug Delivery Reviews, vol. 3. (1989), pp. 67–101.

Rieg–Falson, et al., Characterization of the Enhancing Effect of a Vehicle in a Transdermal System, Drug Development and Industrial (Chm./Abs.), Pharmaceuticals, vol. 112, No. 63 (1990), p. 433.

CA 103:42702 Jane, I, et al, "High–performance liquid chromatographic analysis of basic drugs on silica columns using non–aqueous ionic elements,". *J. Chromatogr* (1985), 323(3), 191–225. Abstract only.

CA 109:48344, Brockkamp et al, "Prodrug behavior of nicotinoyl–morphine derivatives", *J. Pharm. Pharmacol.* (1988), 40(6), 434–7. Abstract only.

*Primary Examiner*—Keith MacMillan
*Attorney, Agent, or Firm*—Pollock, Vande Sande & Priddy

[57] ABSTRACT

Topical composition for transdermal delivery of morphine. The composition contains certain morphine esters in association with a carrier. The compositions relieved pain or tranquilize a mammal when delivered transdermally.

6 Claims, 2 Drawing Sheets

TOPICAL COMPOSITIONS FOR TRANSDERMAL DELIVERY OF PRODRUG DERIVATIVES OF MORPHINE

This application is a 371 of PCT/SE91/00760, filed Nov. 11, 1991, which claims priority to Swedish Application 9003665-8, filed Nov. 16, 1990.

BACKGROUND OF THE INVENTION

1. Field of the Invention

The present invention relates to the use of prodrug derivatives of morphine in effecting transdermal delivery of morphine to the systemic circulation of a mammal.

For purposes of this specification, the term "prodrug" denotes a derivative of morphine which, when administered topically to warm-blooded animals, e.g. humans, is converted into the proven drug, i.e. morphine.

The prodrug forms of morphine of this invention are certain derivatives of morphine which possess a desirable high lipophilicity and biphasic solubility in comparison to the parent compound, morphine, and which are cleaved enzymatically to morphine.

2. Description of the Prior Art

It is generally known and an accepted practice to administer morphine to control chronic pain. Morphine plays a prominent role in the control of pain associated with chronic diseases, especially the chronic pain of cancer, and acute pain, especially the acute pain experienced post-operatively. However, such prior art uses of morphine are subject to serious problems. In addition to the obvious problems associated with potential abuse and addiction, the oral and parenteral administration of morphine for pain control frequently involve wide swings in the pharmacodynamics of the drug over each dosing interval. Furthermore, morphine has a short duration of action and is inefficiently and variably absorbed orally due to first-pass metabolism in the intestine and liver.

During recent years much attention has been paid to the development of transdermal delivery systems as a means of mitigating many of the drawbacks associated with the parenteral or oral route of administration. (Sloan K B, Adv. Drug Delivery Rev. (1989), 67–101) A prerequisite for the development of a transdermal delivery system of morphine and other opioids is, however, that the drugs are capable of penetrating the skin at a sufficiently high rate and are not metabolized during the percutaneous absorption. Morphine which remains the analgesic drug of choice for the treatment of severe pain, unfortunately exhibits, a very limited skin permeability which makes it unsuited for transdermal delivery. For instance, the steady-state flux of morphine through human skin in vitro has been reported to be only 6 $ng/cm^2/h$ when applied in the form of a saturated solution (pH 7.4). (Roy, S. D., and Flynn, G. L., Transdermal delivery of narcotic analgesics: comparative permeabilities of narcotic analgesics through human cadaver skin Pharm. Res. 6 (1989) 825–832). These poor skin-penetration properties of morphine led to the conclusion that morphine is totally unsuited for transdermal delivery. The very poor ability of morphine to permeate into and through the skin can mainly be ascribed to its poor lipophilicity. Thus, the log P value for morphine is only –0.15 where P is the partition coefficient between octanol and aqueous buffer of pH 7.4 (Roy and Flynn 1989). It has now surprisingly been found that transdermal delivery of morphine can be achieved by the prodrug approach proposed in accordance with the present invention.

SUMMARY OF THE INVENTION

The present invention provides novel topical compositions for transdermal delivery comprising an effective amount of a compound represented by the following general Formula I

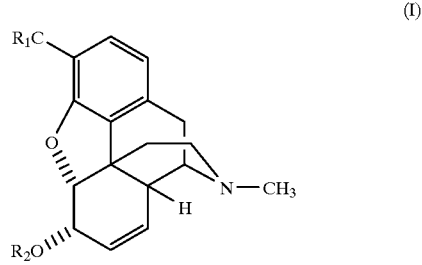

where $R_1$ and $R_2$ are the same or different and are hydrogen and a member selected from the group of physiologically hydrolyzable chemical groups consisting of alkylcarbonyl, alkenylcarbonyl arylcarbonyl, heteroarylcarbonyl, alkoxycarbonyl, aryloxycarbonyl and heteroaryloxycarbonyl groups wherein the alkyl moiety consists of unsubstituted or substituted, straight-chain and branched-chain and cyclic alkyl groups having 1–20 carbon atoms, wherein the alkenyl moiety consists of unsubstituted and substituted, straight-chain and branched-chain and cyclic alkenyl groups having 2–20 carbon atoms, wherein the aryl moiety consists of unsubstituted and substituted phenyl, and phenalkyl groups wherein the alkyl moiety contains 1–3 carbon atoms and the phenyl moiety is unsubstituted or substituted, and the heteroaryl moiety is an aromatic 5- or 6-membered heterocyclic ring containing one or two heteroatoms selected from the group consisting of nitrogen, oxygen, and sulfur; and nontoxic pharmaceutically acceptable acid addition salts thereof, with the proviso that if $R_1$=hydrogen then $R_2 \neq$ hydrogen, and if $R_2$=hydrogen then $R_1 \neq$ hydrogen in association with a topical pharmaceutical carrier for solutions, suspensions, ointments, lotions, creams, gels, pastes, jellies, sprays and aerosols and/or together with a medical device.

The invention also provides a composition containing a non-toxic additive acting as a skin penetration enhancer.

Another subject of the invention is topical dosage forms consisting of a matrix type or reservoir type patch system containing a compound as defined in Formula I or this compound in combination with a penetration enhancing delivery device/process such as iontophoresis. Reservoir type patch systems and iontophoresis are both well known systems for transdermal delivery.

The composition according to the invention can also be combined with an additional drug delivery device such as patches, gauze or compresses.

The invention further includes the use of the esters according to Formula I in the manufacure of a topical medicament for transdermal delivery with the intention of for relieving pain or tranquilizing a mammal and the use of these esters for transdermal delivery.

Also claimed is a process for achieving transdermal delivery of morphine, which comprises applying to mammalian skin an effective amount of a composition according to Formula I.

Examples of suitable straight-chain alkyl groups in Formula I include methyl, ethyl, propyl, butyl, hexyl, heptyl, octyl, dodecyl, palmityl and the like groups.

Examples of suitable branched-chain alkyl groups include isopropyl, sec-butyl, t-butyl, 2-methylbutyl, 2-pentyl, 3-pentyl and the like groups.

Examples of suitable cyclic alkyl groups include cyclopropyl, cyclobutyl, cyclopentyl and cyclohexyl groups.

Examples of suitable "alkenyl" groups include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1–3 carbon atoms" is meant benzyl, phenethyl and phenylpropyl groups wherein the phenyl moiety may be substituted. When substituted, the phenyl moiety of the phenalkyl group may contain independently from 1 to 3 alkyl, hydroxy, alkoxy, halo, amino, mono- and dialkylamino, nitro, carboxyl, alkoxycarbonyl and cyano groups.

Examples of suitable "heteroaryl" are pyridinyl, thienyl or imidazolyl.

As noted herein, the expression "halo" is meant in the conventional sense to include F, Cl, Br, and I.

The term "non-toxic pharmaceutically acceptable acid addition salts" as used herein generally includes the non-toxic addition salts of compounds of Formula I, formed with non-toxic inorganic or organic acids. For example, the salts include those derived from inorganic acids such as hydrochloric, hydrobromic, sulphuric, sulphamic, nitric, phosphoric and the like; and the salts with organic acids such as acetic, propionic, succinic, fumaric, maleic, tartaric, citric, glycolic, lactic, stearic, malic, pamoic, ascorbic, phenylacetic, benzoic, glutamic, salicylic, sulphanilic, methanesulphonic, and the like.

The inventive method for relieving pain and for tranquilizing mammals comprises the application of the above compositions to mammalian skin and in particular, provides for inducing and maintaining analgesia by administering through an area of intact skin a morphine prodrug of the Formula I at an analgetically effective rate and continuing the administration of said material at said rate for an extended period of time at least sufficient to induce analgesia. Said compositions may contain any type of absorption enhancers, such as fatty acids, fatty acid esters and fatty alcohols as well as any type of pharmaceutical additive commonly used for topical or dermal preparations and/or delivery systems such as transdermal patches. It is an object of the present invention to provide an improved method of treating and controlling acute and/or chronic pain.

It is a further object of the present invention to enable pain to be controlled over a sustained period of time by administering transdermally a morphine prodrug of Formula I.

According to the present invention, the permeability coefficients and fluxes of the compounds and compositions through mammalian skin tissue are established as being sufficient in magnitude to be practical for direct transdermal applications, producing time-sustained dosage rates consistent for pain suppression and tranquilizing effects over prolonged periods of time.

The morphine prodrug derivatives of the present invention are certain derivatives which show a higher lipophilicity and biphase solubility than the active parent drug and hence are better able to penetrate the skin of a human or non-human animal and which are capable of reverting to the active morphine during or after transportation through the skin. These characteristics make the derivatives useful for transdermal delivery of morphine.

Figure 1:
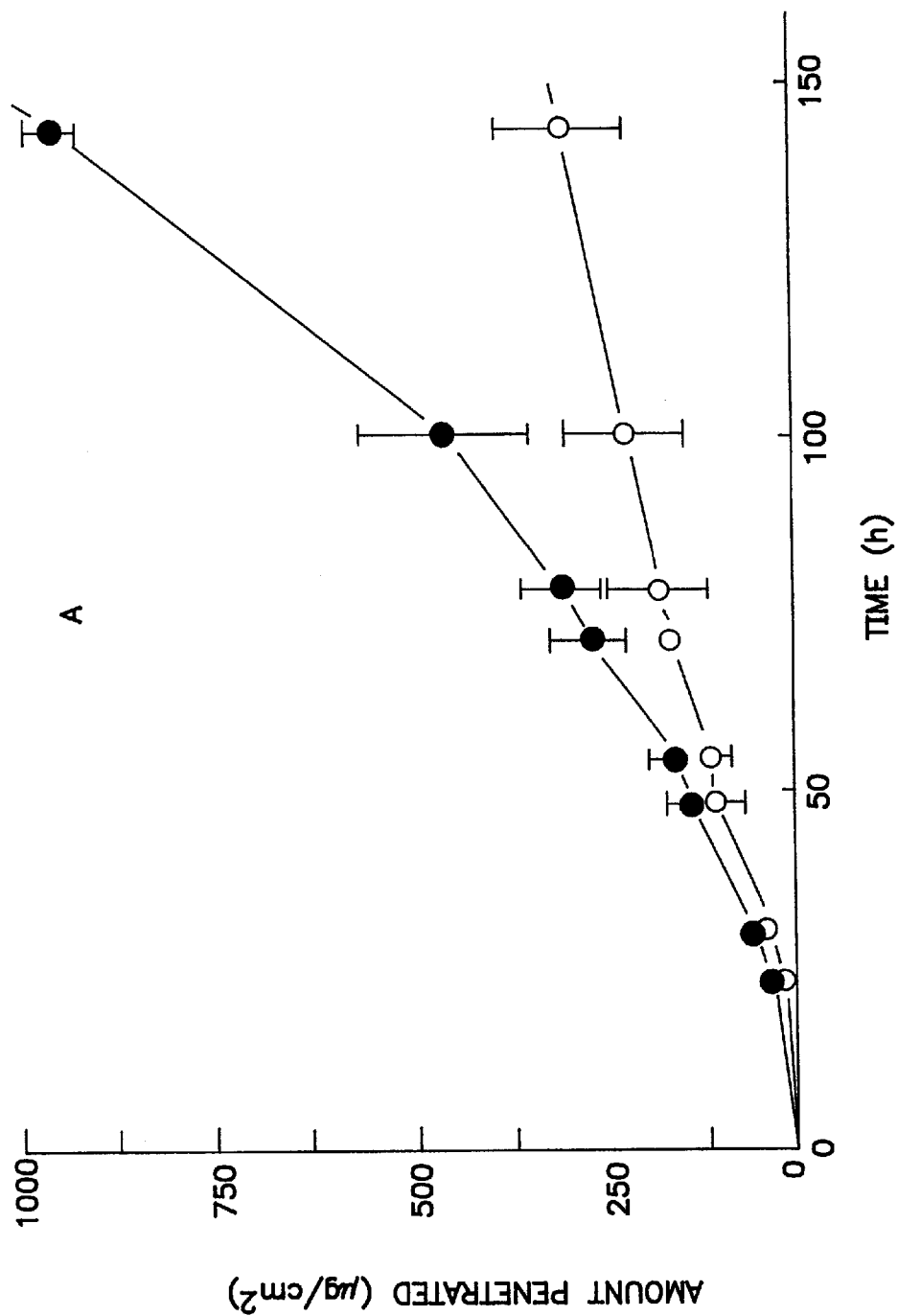
FIGS. 1 and 2 show the permeability of some morphine esters through human skin. The amount of morphine appearing in the receptor phase is plotted as a function of time from suspensions or solutions of 3,6-dipropionyl morphine (A), (FIG. 1) and dihexanoyl morphine (B), (FIG. 2) in 0.05 M phosphate buffer of pH 7.0 (O) and isopropyl myristate(•).
Figure 2:
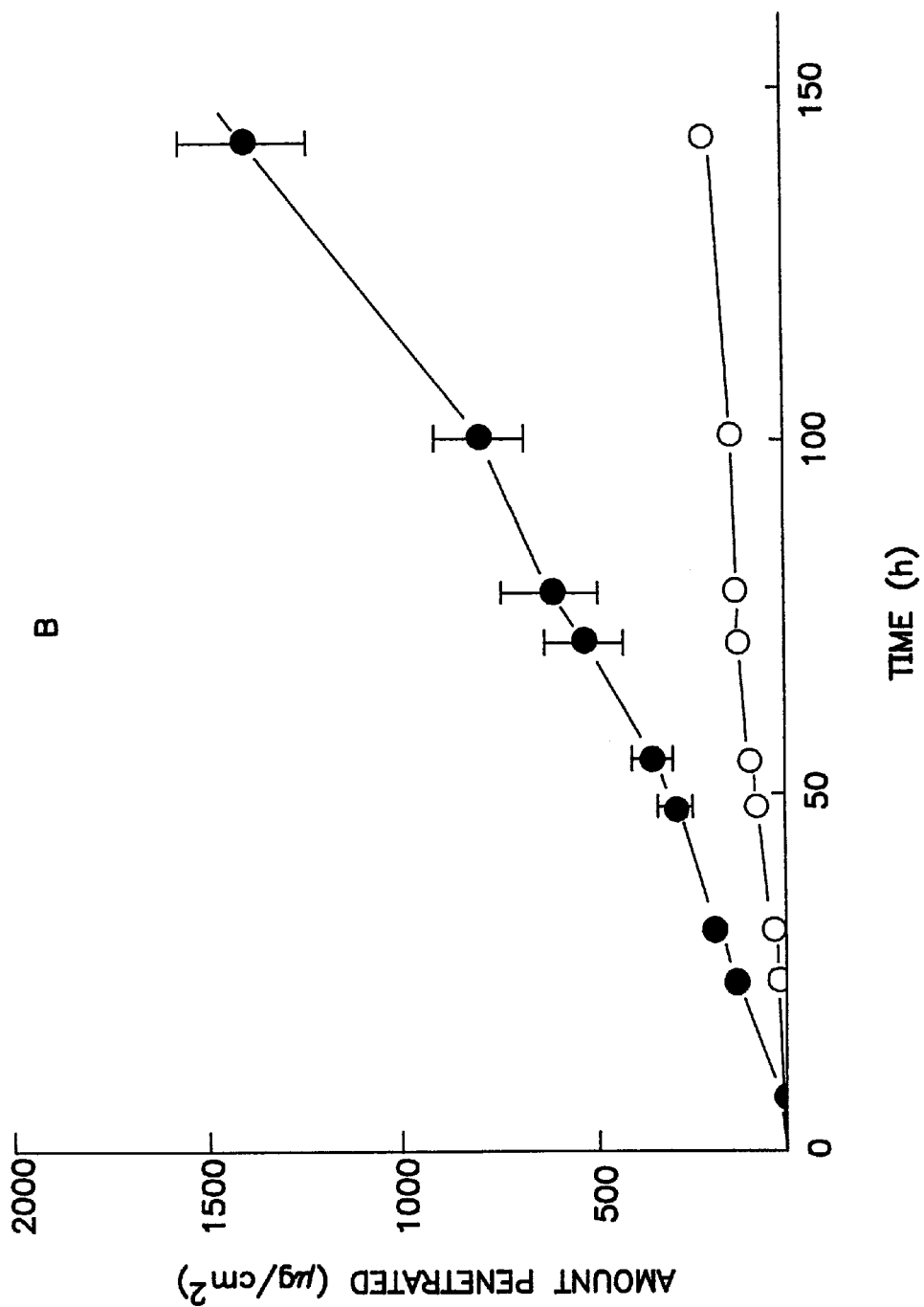

3,6-Dipropionyl morphine was applied in the form of suspensions in both buffer and IPM whereas 3,6-dihexanoyl morphine was applied in buffer and as a solution (200 mg/ml) in IPM.

DETAILED DESCRIPTION OF THE INVENTION

Among the compounds represented by the general Formula I, preferred compounds are such in which $R_1$ and $R_2$ are the same and is one of the following groups:

acetyl
propionyl
butyryl
valeryl
hexanoyl
isobutyryl
methoxyacetyl
ethoxyacetyl
benzoyl
nicotinoyl
methoxycarbonyl
ethoxycarbonyl
propoxycarbonyl
butoxycarbonyl
hexyloxycarbonyl
octyloxycarbonyl
imidazolylcarbonyl Other preferred compounds are such in which $R_1$ is hydrogen and $R_2$ is one of the groups listed above, or $R_2$ is hydrogen and $R_1$ is one of these groups.

The compounds of Formula I are esters (carboxylic acid or carbonate esters) of morphine formed either at $C_3$ or $C_6$, or at both hydroxyl groups. Several esters of morphine have long been known including the 3,6-diacetyl ester (heroin) and 3,6-dinicotinoyl ester (nicomorphine). Information on the preparation or pharmacological activity of various esters of morphine can thus be found in the following references: Beckett and Wright (1875), Hesse (1884), Merck (1899), Emde (1930), Mannich and Siewert (1939), Welsh (1954), Zirm and Pongratz (1959), Pongratz and Zirm (1957, 1964), Voldeng et al. (1968), Selmeci et al. (1968), Borowitz and Diakiw (1975), May and Jacobsen (1977), Andrew et al. (1984), Owen et al. (1984), Sy et al. (1986), Broekkamp et al. (1988) and Whitehouse et al. (1990). See reference list on page 12.

However, these references or other information in the literature do not disclose or indicate any utility of esters or other derivatives of morphine as prodrug forms suitable for transdermal delivery of morphine, nor any properties of the compounds that might indicate such utility.

As will be described below it has now surprisingly been found that compounds of Formula I—in contrast to morphine itself—are highly useful to achieve transdermal delivery of morphine at an analgetically effective rate and extent. Preparation of Compounds of Formula I The compounds of Formula I can be prepared by various methods as already described in the literature for a number of morphine esters (see the references cited above). Thus, we prepared 3,6-dipropionyl, 3,6-diisobutyryl and 3,6-dihexanoyl morphine by reacting morphine with an excess of the corresponding acid anhydride, following the method described by Owen et al.

6-Propionyl morphine was prepared as described by Sy et al. and the 3-propionyl, 3-isobutyryl and 3-hexanoyl esters as described by Welsh.

Detailed descriptions of the preparation of some morphine esters are given in Examples 1–5.

EXAMPLE 1

3,6-dipropionyl morphine (Formula I, $R_1=R_2=C_2H_5CO$)

A mixture of morphine (2.0 g) and propionic anhydride (5.0 ml) was stirred at 90° C. for 4 h. Upon cooling to room temperature water (40 ml) was added. After 1 h the solution was partitioned between ether (50 ml) and 10% potassium hydroxide solution (40 ml). The ether phase was separated, washed with water, dried over anhydrous sodium sulphate and evaporated in vacuo. The residue obtained was crystallized form ethanol-water to yield 2.7 g of the title compound, m.p. 106–107° C.

EXAMPLE 2

3-propionyl morphine (Formula I, $R_1=C_2H_5CO$, $R_2=H$)

Propionic anhydride (13.1 ml, 100 mmol) was added while stirring to a mixture of sodium bicarbonate (20 g, 240 mmol) and morphine hydrochloride (3.75 g, 10 mmol) in water (200 ml). After complete addition the mixture was stirred for 90 min and extracted with chloroform (2×100 ml). The combined extracts were dried over anhydrous sodium sulphate and evaporated in vacuo to yield the title compound as a colorless oil in 95% yield. The compound crystallized from petroleum ether at −18° C., m.p. 85–86° C. (Anal.: calc./w $C_{20}H_{23}NO_4$: C,70.36; H,6.79; N,4.10. Found: C,70.35; H,6.89, N,4.19.). The hydrochloric acid salt of the compound was prepared by adding a methanolic HCl solution to a solution of the base in ether, m.p. 157–158° C. (monohydrate).

EXAMPLE 3

3,6-diisobutyryl morphine (Formula I, $R_1=R_2=(CH_3)_2CH_2CO$)

The compound was prepared essentially as described in Example 1, using isobutyric anhydride instead of propionic anhydride. The compound was recrystallized from ether-petroleum ether, m.p. 96–97° C.

EXAMPLE 4

3,6-dihexanoyl morphine (Formula I, $R_1=R_2=CH_3(CH_2)_4CO$)

The compound was prepared essentially as described in Example 1, using hexanoic anhydride instead of propionic anhydride. The compound was a colorless oil.

EXAMPLE 5

3-hexanoyl morphine (Formula I, $R_1=CH_3(CH_2)_4CO$, $R_2=H$)

The compound was prepared essentially as described in Example 2, using the equivalent amount of hexanoic anhydride instead of propionic anhydride. The compound was a colorless oil.

Solubility and Lipophilicity of Morphine Esters

The solubility of the compounds, given in Examples 1–5, in water at pH 7 and in isopropyl myristate and their partition coefficients between octanol and pH 7.4 aqueous buffer (P) are shown in Table 1. The experimental methods used for these determinations are described below.

TABLE 1

Solubilities and partition coefficients (P) of morphine and various ester prodrugs at 21° C.

| Compound | log P[a] | Solubility (mg/ml) In water at pH 7.0 | In IPM[b] |
|---|---|---|---|
| Morphine. | −0.06 | 1.8 | 0.023 |
| 3-Propionyl-morphine | 0.66 | 21 | 79 |
| 3,6-Dipropionyl-morphine | 1.66 | 3.6 | 41 |
| 3-Hexanoyl-morphine | 2.04 | 2.6 | >150 |
| 3,6-Diisobutyryl-morphine | 2.60 | 0.6 | 80 |
| 3,6-Dihexanoyl-morphine | >4 | 0.02 | >200 |

[a]Between octanol and pH 7.4 aqueous buffer.
[b]IMP: Isopropyl myristate

The solubilities of morphine and morphine esters were determined in triplicate in a phosphate buffer solution of pH 7.0 and in isopropyl myristate (IPM) at 21° C. by placing excess amounts of the compounds in 5 ml of the solvent. The mixtures were placed in an ultrasonic bath for 10 min and then rotated on a mechanical spindle for 24 h and filtered. After rotation for 1 h the pH of the phosphate buffer mixtures was adjusted to 7.0. An aliquot of the filtrates was diluted with water or acetonitrile and analyzed by HPLC.

The apparent partition coefficients (P) of morphine and the various esters were determined at 21° C. in an octanol-0.02 M phosphate buffer (pH 7.4) system. The concentration of the compounds in the aqueous phase before and after partitioning was determined by HPLC analysis, and the partition coefficients determined.

From the data shown in Table 1 it can readily be seen that the morphine esters are more lipophilic than the parent drug in terms of octanol-aqueous buffer partition coefficients. It is also apparent that morphine esters showing both increased water and lipid solubility relative to morphine can be obtained. This higher biphasic solubility may be most favourable for skin penetration.

Skin Permeation Studies

The feasibility of achieving transdermal delivery of morphine via the prodrugs of the present invention was evaluated by diffusion experiments in vitro using human skin samples.

Whole abdominal human skin obtained under autopsy from two donors was used. The skin was stored at −18° C. and was allowed to thaw gradually at room temperature before use. All subcutaneous fat was removed and the skin cut into pieces. The excised skin was mounted in open Franz diffusion cells. They have an available diffusion area of 0.70 $cm^2$.

The dermal side of the skin was exposed to the receptor medium (7.5 ml of 0.05 M isotonic phosphate buffer of pH 7.2) which was stirred magnetically and kept at a constant temperature of 37° C. with a circulating water bath.

The compounds studied were applied as solutions or suspensions (200 microliter) in an aqueous buffer (pH 7.0) or in isopropyl myristate (IPM).

The suspensions were stirred for 24 h prior to application to the skin surface. Samples of 2 ml were removed from the receptor phase and replaced with fresh buffer at appropriate intervals. The samples were stored at −20° C. until analyzed for their morphine, di- and/or monoester content by HPLC as described below. The permeation studies of each compound were done in tri- or quadruplicate. Reversed-phase HPLC procedures were used for the quantitative determination of morphine and its esters. A deactivated Supelcosil column was eluted with a mobile phase consisting of a mixture of acetonitrile (15–70% v/v) and 0.01 M phosphate buffer solution of pH 6.5. The concentration of acetonitrile was adjusted for each compound to give a suitable compound retention time (3–10 min). The flow rate was 1.0 ml/min and the column effluent was monitored at 215 or 280 nm. It was assured that in each case adequate separation of the ester from morphine and monoesters (in the case of the diesters) was achieved. Quantitation of the compounds was done from measurements of the peak heights in relation to those of standards chromatographed under the same conditions.

In the case of morphine no measurable amounts of drug could be detected in the receptor phase during diffusion experiments lasting up to 200 h. The failure of morphine to penetrate human skin from the vehicles applied in significant amounts is in accordance with the results obtained by Roy and Flynn (1989). These authors reported a steady-state flux of 0.006 $\mu$g /cm$^2$/h for the permeation of morphine through human skin from a saturated solution of the drug in a pH 7.4 buffer.

In contrast, the 3-hexanoyl, 3,6-dihexanoyl and other 3,6-dipropionyl morphine esters readily penetrated human skin. The results obtained with some of these derivatives are shown in FIG. 1 in which the cumulative amounts (in mg morphine base) of morphine or ester measured in the receptor phase divided by the surface area of the diffusion cell are plotted against the time of sampling. The steady-state fluxes were obtained from the slopes of the linear portions of these plots. The permeability coefficients (Kp) for the steady-state delivery were obtained by dividing the steady-state fluxes by the solubilities or concentrations of the compounds in the vehicle applied. The values obtained for various morphine esters, using morphine as a reference, are given in Table 2.

Thus, the 3-hexanoyl ester afforded a more than 2,000-fold higher flux relative to morphine itself when delivered from an aqueous buffer vehicle, and progressevly greater enhancement was achieved when isopropyl myristate was used as a vehicle. The increased solubility of the esters in the vehicles (Table 1) combined with expected concomitant example, for transdermal delivery is 25 cm$^2$ and if a flux of 25 microgram/h/cm$^2$ is used (see Table 2), it would be possible to deliver 0.625 mg morphine/h or 15 mg over 24 h. This amount is higher than that usually administered (10 mg) parenterally during 24 hours.

The actual administration or use of the transdermal analgesic compositions according to the present invention can be in any conventional form and may follow any of the methods generally known to the art. For instance, the active narcotic analgetic compound (i.e., a morphine prodrug of Formula I) can be used in association with any pharmaceutical dosage form such as, for example, but not limited thereto, any solution, ointment, lotion, paste, jelly, gel, cream, spray or aerosol generally known to the art. As such, the narcotic analgetic prodrug form in association with the pharmaceutical dosage form can be used directly as a topical composition or used in combination with an additional drug delivery device, for example, but not limited thereto, patches, gauze, compresses, or the like, again, as generally known in the art. The dosage forms may contain any type of absorption enhancers such as fatty acids, fatty acid esters and fatty alcohols or any other non-toxic compounds which are known to increase skin permeability. In particular, the transdermal analgesic compositions, can be administered in the form of a patch wherein, the active morphine prodrug agent is present in a polymeric matrix or in a reservoir system combined with a polymeric rate controlling membrane.

TABLE 2

Fluxes and permeability coefficients (Kp) for steady-state phase of delivery of morphine through human skin from isopropyl myristate (IPM) and an aqueous buffer of pH 7.0

| Compound | Flux ($\mu$g/cm$^2$/h) | | Kp (cm/h) | |
| --- | --- | --- | --- | --- |
| | IMP | Buffer | IPM | Buffer |
| Morphine | <0.01 | <0.01 | <4.3 × 10$^{-4}$ | <5.6 × 10$^{-6}$ |
| 3,6-Dipropionyl-morphine[a] | 8.7 ± 0.4 | 2.5 ± 0.5 | 3.0 × 10$^{-4}$ | 1.0 × 10$^{-3}$ |
| 3,6-Dihexanoyl-morphine | 11.7 ± 1.2[b] | 1.7 ± 0.2 | >1.6 × 10$^{-4}$ | 0.14 |
| 3-Hexanoyl-morphine | 35.6 ± 12.0[c] | 25.3 ± 4.2 | >2.4 × 10$^{-4}$ | 1.3 × 10$^{-2}$ |
| 3-Proprionyl-morphine | 37.7 ± 4.1 | | | |
| 3-Acetyl-morphine | 11.4 ± 1.8[b] | | | |
| 3-Isobutyryl-morphine | 27.0 ± 3.3[b] | | | |
| 3-Valeryl-morphine | 16.5 ± 2.7[b] | | | |
| 3-Butoxy-morphlne | 8.3 ± 2.2[b] | | | |

[a]Approximately 50% of the amounts penetrated were present in the receptor phase as morphine and 50% as the 6-monoester. The flux values given were calculated in terms of total morphine equivalents.
[b]The IPM solution applied was not saturated. It contained the compound at a concentration of 200 mg/ml
[c]The IPM soiution applied was not saturated. It contained the compound at a concentration of 125 mg/ml
For all cases except the 3,6-diproprionyl ester, only morphine was found in the receptor phase, whereas for the 3,6-dipropionyl ester approximately 50% of the amounts penetrated were present in the receptor phase as morphine and 50% as the corresponding 6-monoester. It is of great interest to note the appreciable skin enzyme-mediated hydrolysis of the esters during diffusion.

An experiment with 3-Proprionyl-morphine dissolved in ethanol-water (3:1 vol/vol) at a concentration of 620 mg/ml revealed a flux of 102±8.0 $\mu$g/cm$^2$/h.

The results obtained from the human skin permeation experiments show that it is possible to a very high degree improve the skin penetration of morphine via prodrugs.

Reference List
Andrew, R., Tasker, R. and Nakatsu, K.
  Evaluation of 3,6-dibutanoylmorphine as an analgesic in vivo: comparison with morphine and 3,6-diacetyl morphine.
  Life Sci. 34 (1984) 1659–1667

Beckett, G. H. and Wright, C. R. A.,
Action of the organic acids and their anhydrides on the natural alkaloids. Part II.
J. Chem. Soc. 28 (1875) 15–26

Borowitz, I. J. and Diakiw, V.,
The preparation and synthetic utility of O-substituted normethylmorphines.
J. Heterocycl. Chem., 12 (1975) 1123–1126.

Broekkamp, C. L., Oosterloo, S. K. and Rijk, H. W.,
Prodrug behaviour of nicotinoylmorphine esters.
J. Pharm. Pharmacol. 40 (1988) 434–437.

Emde, H.,
Über Diastereomerie VI. Konfiguration der Morphinalkaloide.
Helv. Chim. Acta, 13 (1930) 1035–1058.

Hesse, O.,
Studien über Morphin.
Ann. Chem., 222 (1884). 203–234.

Mannich, C. and Siewert, G., Über 6-Benzoyl-morphin.
Arch. Pharm., 277 (1939) 128–130.

May, E. L. and Jackson, A. E.,
Chemistry and pharmacology of homologs of 6-acetyl and 3,6-diacetylmorphine.
J. Pharm. Sci., 66 (1977) 285–286.

Merck, E.,
Ueber einige Morphinderivate.
Arch. Pharm., 237 (1899) 211–222.

Owen, J. A., Elliot, J., Jhamandas, K., and Nakatsu, K.,
Morphine diesters, I. Synthesis and action on guinea pig ileum.
Can. J. Physiol. Pharmacol., 62 (1984) 446–451.

Pongratz, A. and Zirm, K. L.,
Verfahren zur Darstellung des neuen 6-Morphin Mononicotinsaureesters.
Osterr. Patentschrift Nr. 234,914 (1964).

Pongratz, A. and Zirm, K. L.,
Monatsh., 88 (1957) 330.

Selmeci, G., Szlavik, L., Kaskoto, Z., Lepenyene, J. M. and Tothne, A. I.,
Synthesis of new derivatives of morphine. II. Production of benzoylmorphines with analgesic action and benzylmorphine possessing morphine-potentiating activity.
Khim. Farm. Zh., 2 (7) (1968) 19–23

Sy, W. -W., By, A. W., Neville, G. A. and Wilson, W. L.,
Syntheses of 3-O- and 6-O-propanoylmorphine—a reinvestigation and correction.
J. Pharm. Sci., 75 (1986) 787–789.

Voldeng, A. N., Brandley, A., Kee, R. D., King, E. L. and Melder, F. L.,
Synthesis of adamantyl analoga of analgesics.
J. Pharm. Sci., 57 (1968) 1053–1055.

Welsh, L. H.,
O3-Monoacetylmorphine.
J. Org. Chem., 19 (1954) 1409–1415.

Whitehouse, L. W., Paul, C. J., Gottschling, K. H., Lodge, B. A. and By, A. W.,
Antinociceptive activity of propionyl esters of morphine: a reevaluation.
J. Pharm. Sci., 79 (1990) 349–350.

Zirm, K. L. and Pongratz, A.,
Zur Wirkung des Pyridin-3-Carbonsäurebiesters des Morphines als Analgeticum.
Arzneim.-Forsch., 9 (1959) 511–513.

It is claimed:

1. A process for achieving transdermal delivery of morphine comprising applying to mammalian skin an effective amount of a topical composition for said transdermal delivery of morphine comprising an effective amount of a compound of the formula:

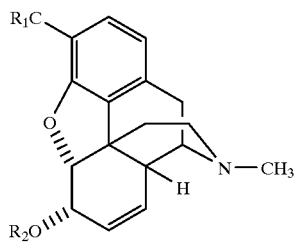

(I)

wherein a) $R_1$ is a member selected from the group of physiologically hydrolyzable chemical groups consisting of propionyl, isobutyryl, and hexanoyl, b) and $R_2$ is hydrogen, and nontoxic pharmaceutically acceptable acid addition salts thereof, in association with a topical pharmaceutical carrier to thereby provide solutions, suspensions, ointments, lotions, creams, gels, pastes, jellies, sprays and aerosols.

2. The process of claim 1 wherein said transdermal delivery is effected by iontophoresis.

3. The process of claim 1 wherein $R_1$ is propionyl.

4. The process of claim 1 wherein $R_1$ is isobutyryl.

5. The process of claim 1 wherein $R_1$ is hexanoyl.

6. The method of claim 1 wherein said topical composition contains isopropyl myristate as a carrier.

* * * * *